US006992280B2

(12) United States Patent
White et al.

(10) Patent No.: US 6,992,280 B2
(45) Date of Patent: Jan. 31, 2006

(54) TEST OBJECT FOR CALIBRATION OF IMAGING MEASUREMENTS OF MAMMALIAN SKELETAL JOINTS

(75) Inventors: David L. White, Oakland, CA (US); Manish Kothari, San Francisco, CA (US); Richard A. Carano, San Ramon, CA (US)

(73) Assignee: Synarc, Inc., Maynard, MA (US)

( * ) Notice: Subject to any disclaimer, the term of this patent is extended or adjusted under 35 U.S.C. 154(b) by 314 days.

(21) Appl. No.: 10/388,118

(22) Filed: Mar. 12, 2003

(65) Prior Publication Data

US 2004/0005035 A1 Jan. 8, 2004

Related U.S. Application Data

(60) Provisional application No. 60/370,019, filed on Apr. 4, 2002.

(51) Int. Cl.
*G01D 18/00* (2006.01)

(52) U.S. Cl. .................. 250/252.1; 378/207; 324/300; 73/1.86

(58) Field of Classification Search ............. 250/252.1; 378/207; 324/300; 73/1.86
See application file for complete search history.

(56) References Cited

U.S. PATENT DOCUMENTS

| | | | | | |
|---|---|---|---|---|---|
| 3,714,428 | A | * | 1/1973 | Gasaway | 378/163 |
| 4,538,071 | A | * | 8/1985 | Bardoux et al. | 250/505.1 |
| 4,618,826 | A | * | 10/1986 | Smith et al. | 324/308 |
| 4,818,943 | A | * | 4/1989 | Chandra | 324/318 |
| 5,299,253 | A | * | 3/1994 | Wessels | 378/163 |
| 5,312,755 | A | * | 5/1994 | Madsen et al. | 436/8 |
| 5,416,816 | A | * | 5/1995 | Wenstrup et al. | 378/18 |
| 5,976,066 | A | * | 11/1999 | Yanch et al. | 600/1 |
| 6,302,582 | B1 | * | 10/2001 | Nord et al. | 378/207 |
| 6,318,146 | B1 | * | 11/2001 | Madsen et al. | 73/1.86 |
| 6,901,280 | B2 | * | 5/2005 | Pelletier et al. | 600/410 |
| 2002/0170339 | A1 | * | 11/2002 | Passi et al. | 73/1.86 |

* cited by examiner

*Primary Examiner*—Albert Gagliardi
(74) *Attorney, Agent, or Firm*—Townsend and Townsend and Crew LLP

(57) ABSTRACT

The invention provides a test device or "phantom" for use in conjunction with medical imaging modalities. The phantom mimics the properties of joint particular cartilage. The phantom is useful for quality assurance of images of joints obtained using an array of medical imaging modalities.

11 Claims, 4 Drawing Sheets

End View

Top View

End View

Top View

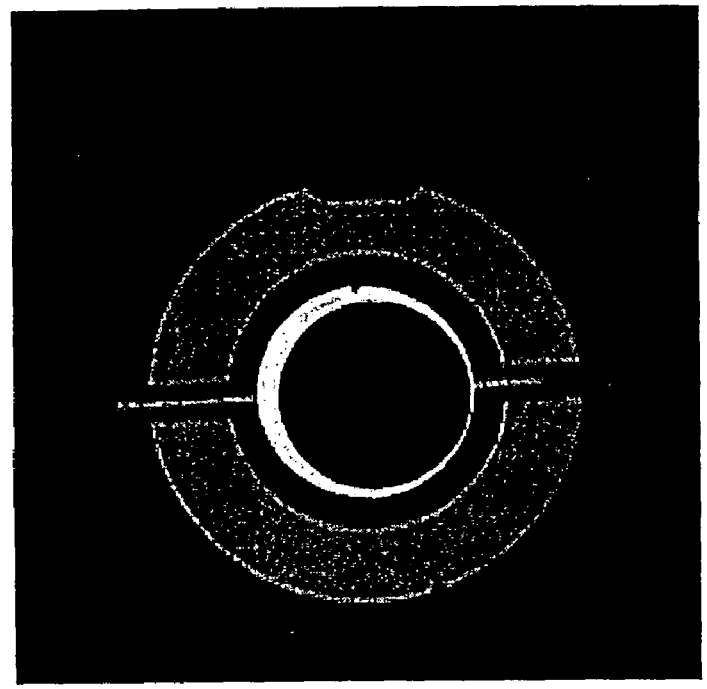
End view  FIG. 4A
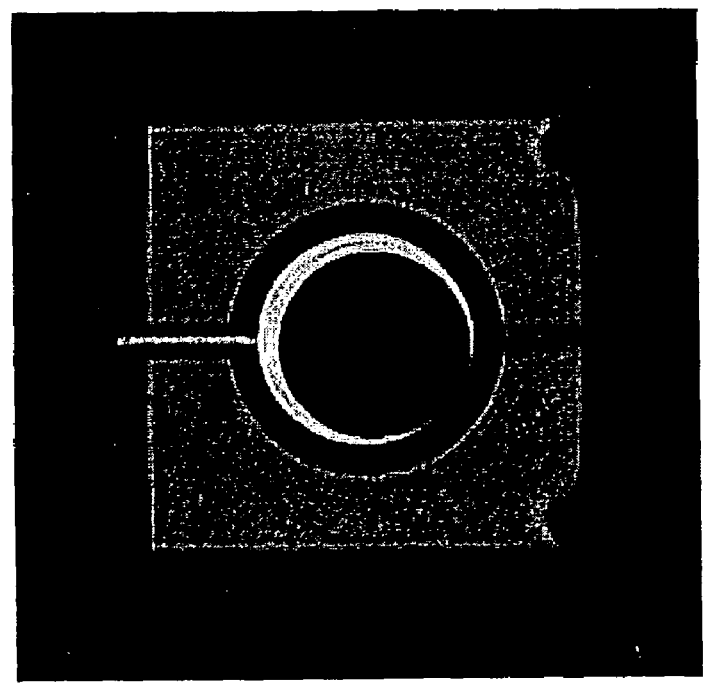
Top View  FIG. 4B

TEST OBJECT FOR CALIBRATION OF IMAGING MEASUREMENTS OF MAMMALIAN SKELETAL JOINTS

CROSS-REFERENCES TO RELATED APPLICATIONS

This application claims priority to U.S. Provisional Patent Application Ser. No. 60/370,019, filed on Apr. 4, 2002, the disclosure of which is incorporated herein by reference in its entirety for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

A phantom is a device that simulates a body of tissue in its interaction with radiation. Various types of phantoms are used to test the performance of medical imaging equipment by mimicking the radiation attenuation and absorption properties of human tissue. Phantoms are also used to measure radiation dosage during therapy, for teaching purposes, to calibrate imaging equipment and for research. Phantoms are an essential element of maintaining high therapeutic and diagnostic quality assurance and control. When applied to image quality control, phantoms are used to measure system resolution, focal spot size, contrast, exposure controls, image artifacts, etc.

Two classes of phantoms are widely used. One type of phantoms uses plastics, gels, water and other chemical mixtures to simulate human tissue and organs. These devices are referred to as "tissue equivalent." The other type of phantoms generates test patterns for confirming and evaluating system performance.

Numerous devices for marking, calibrating and aligning images from CAT and MRI systems are known in the art. For example, U.S. Pat. No. 5,299,253 of Wessels describes an alignment system and method to uniquely identify a cross-section of an imaged object to facilitate correlation of images. This is especially useful in identifying lesions near organs where a tumor may be obscured by an adjacent organ. It is, however, unrelated to the objective of this invention. U.S. Pat. No. 5,416,816 of Westrup describes a calibration template for computed radiography. It includes a variety of elements which simulate the X-ray absorption characteristics of various human body portions and organs. This device is useful for training radiologists and facilitates standardization of CAT image quality, which is especially useful for remote analysis of transmitted radiographic digital data. This device is of little use in assessing accuracy of table movements, however. U.S. Pat. No. 3,714,428 of Gasaway discloses a marker for radiology. A radiolucent member having stepped sloping edges with radio-opaque numerals is used to automatically record the height of the visible plane appearing on the film relative to a reference surface. The image of the numeral located closest to the plane is visible on the film while the remaining indicia are obscured.

Most MR imaging centers have some form of machine and image quality control that ensures that the acquired images are of sufficient quality for clinical evaluation. Test objects ("phantoms") are often used for this purpose, and a number of investigators have described their application to determinations of the accuracy of volumetric measurements (Tofts et al., *Magn Reson Imaging* 1997; 15(2):183–92), resolution (Fellner et al. *Magn Reson Imaging* 2001 July; 19(6):899–904), and relaxation time measurements (Laubach et al., *J. Magn. Reson. Imaging* 1998 8(6):1349–54; Fellner et al., supra; and Kjaer et al., *Acta Radiol.* 1987 May–June; 28(3):345–51). Phantoms have also been used to determine the longitudinal (Firbank et al., *Br. J Radiol.* 2000 April; 73(868):376–83) and inter-site (Barker et al., *Magn. Reson. Imaging* 1992; 10(4):585–95) stability of many of these measures. Phantoms typically have been made of acrylic (Tofts; Firbank; and Fellner, supra), or other non-metallic materials (Tofts, supra; Luft et al., *J. Magn. Reson. Imaging* 1996 July–August; 6(4):700–4; Disler et al., *Invest. Radiol.* 1994 August; 29(8): 739–45; and Laubach et al., *J. Magn. Reson. Imaging* 1998 November–December; 8(6):1349–54), and filled with water (Tofts; and Disler, supra), aqueous solutions of paramagnetic ions (Tofts; Luft; Disler; Laubach; Firbank; Fellner; Kraft et al., *Magn. Reson. Med.* 1987 December; 5(6): 555–62; and Kjaer et al., *Acta Radiol.* 1987 May–June; 28(3):345–51), gels (Lufts; Laubach; Kraft; and Kjaer, supra), vegetable oil (Disler, supra), and other materials that produce an MRI signal. These phantoms incorporate a number of shapes and configurations depending upon their purpose. Among these are cylinders (Tofts; Luft; Disler; and Fellner, supra) cones (Firbank, supra; and Coffey et al., *Med. Phys.* 1989 March–April; 16(2): 273–8), spheres (Disler; and Firbank, supra), and irregular (Lufts; Disler and Lauback, supra) or deformable compartments constructed of, for example rubber (Disler; and Laubach, supra).

None of the prior phantoms are well suited for the assessment of quantitative measures of joint cartilage, especially because of they inadequately model cartilage curvature and thinness. Surprisingly, the present invention provides a phantom that is ideally suited for quality control of images of joints and joint cartilage.

BRIEF SUMMARY OF THE INVENTION

Magnetic Resonance Imaging (MRI) has been used for some time to assess the status of joints, particularly the knee, in a variety of clinical circumstances, including osteoarthritis (Stoller D W in "Clinical Magnetic Resonance Imaging", Edelman R R, Heslink J R, Slatkin M B, eds, W. B.Saunders Co., Philadelphia, $2^{nd}$ edn, 1996, Chap. 61 "Knee", p1954–2003). MRI of the knee provides excellent visualization of all aspects of the knee joint, including cartilage, synovium and subchondral bone (FIG. 1). This visualization capability combined with the three dimensional tomographic nature of MRI makes it a favorable technology for use in the evaluation of osteoarthritis. In particular, cartilage volume and cartilage T2 measurements made from MR images acquired at over time may provide a quantitative measure to assess disease status and response to therapy in this slowly progressing degenerative disease. An understanding of the precision of these measures is necessary to be able to design studies involving the longitudinal assessment of degenerative change in the knee in clinical trials (Peterfy C G, *Semin. Musculoskelet. Radiol.* 2001 December; 5(4):365–78).

A test object ("phantom") has been constructed, which allows the determination of the longitudinal accuracy and precision of the quantitative measurements of joint cartilage volume and thickness. The phantom of the invention includes an offset sphere-within-a-sphere configuration that produces a three-dimensional space that models critical aspects of joint articular cartilage, specifically, its thickness and curvature. Because the phantom has a regular and well-defined shape, it can be precisely described using simple geometric formulae.

Thus, in a first aspect, there is provided a phantom comprising:

(a) a housing having an outside surface, an inside surface and a central axis defining a hollow region therein;

(b) a hollow sphere oriented within the hollow region of the housing, having an inside surface defining a hollow spherical region therein;

(c) a second sphere oriented inside the hollow sphere, anchored at one point to the inside surface of said hollow sphere, the second sphere having an outside surface defining a hollow region between the outside surface of the second sphere and the inside surface of the hollow sphere; and (d) a stabilizing member joining the hollow sphere and the housing, the stabilizing member having a central axis defining a hollow region therein which communicates with the outside surface of the housing and the hollow region of the hollow sphere.

Other aspects, objects and advantages of the invention will be apparent from the detailed description that follows.

BRIEF DESCRIPTION OF THE DRAWINGS

FIG. 4 shows MR images of an exemplary phantom of the invention: (A) end view; (B) top view.

DETAILED DESCRIPTION OF THE INVENTION

Figure 1:
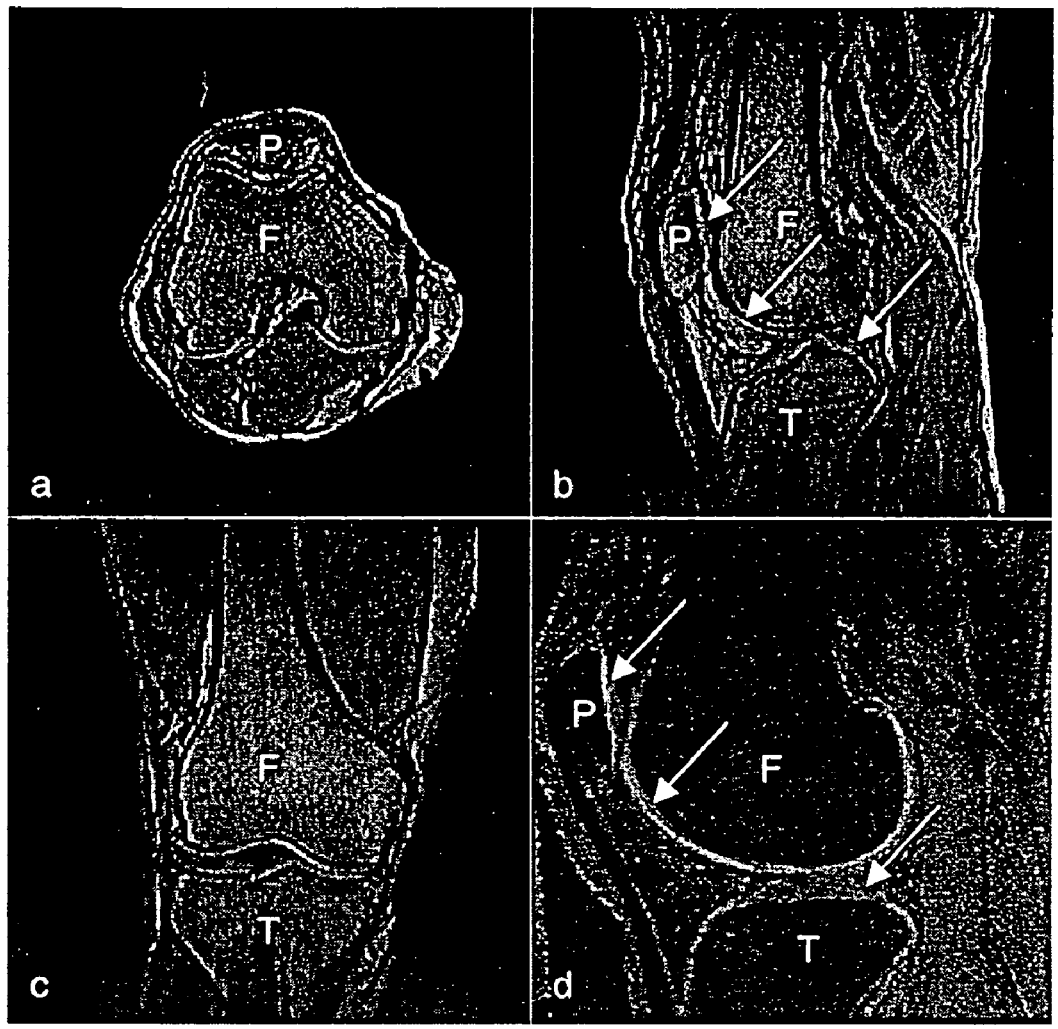
FIG. 1 shows magnetic resonance images of a human knee: a), b), and c) are axial, sagittal, and coronal, respectively, T1-weighted images showing the overall anatomy, with femur (F), patella (P), tibia (T), and articular cartilage (arrows) indicated. Panel d) is one sagittal slice from a set of 3-D gradient-recalled-echo images in which the high signal due to fat has been selectively attenuated ("fat saturation") so that bone marrow is relatively hypointense and articular cartilage is hyperintense (cf. a)–c))

The present invention provides a test object ("phantom") useful for determining the longitudinal accuracy and precision of the quantitative measurements of joint cartilage volume and thickness. The phantom includes an offset sphere-within-a-sphere configuration that produces a three-dimensional space that models critical aspects of joint articular cartilage, specifically, its thickness and curvature. Because the phantom has a regular and well-defined shape, it can be precisely described using simple geometric formulae.

Thus, in a first aspect, the present invention provides a phantom. The phantom includes a housing having an outside surface, an inside surface and a central axis defining a hollow region therein. Inside the housing is a hollow sphere. The hollow sphere has an inside surface that defines the hollow space within the sphere. A second sphere is located within the hollow sphere, anchored at a point to the inside surface of the hollow sphere. The diameter of the second sphere is smaller than that of the hollow sphere, thus, the outer surface of the second sphere and the inner surface of the hollow sphere define a hollow region between these two surfaces. The hollow sphere is attached to the housing by means of a stabilizing member that runs from the housing member to the outside surface of the hollow sphere.

The second sphere is either hollow or solid. When the second sphere is hollow, it can be air-filled or it may contain a gel, a solution or a suspension as is described for the hollow sphere in the sections below. The hollow sphere and the second sphere, optionally contain either the same material or a different material.

In a presently preferred embodiment, the stabilizing member is a hollow tube that communicates with the outside surface of the housing and the inside surface of the hollow sphere. The arrangement of the hollow tube in relation to the other components of the device allows a means for adding a liquid to, or removing it from the hollow sphere of the device. One of skill will appreciate that multiple solid or hollow tubes in any configuration can be utilized as support members for the hollow sphere.

In another preferred embodiment, the hollow region of the hollow sphere contains a gel (e.g., agarose), or a liquid. The gel or liquid can include a dissolved or suspended contrast agent. The liquid is preferably a member selected from water (e.g., distilled water), a solution of a contrast enhancing agent, a suspension of a contrast enhancing agent and combinations thereof.

When the phantom of the invention includes a contrast enhancing agent, it is well within the abilities of one of skill to select an appropriate contrast agent and an appropriate concentration of the contrast agent for a given application. Exemplary phantoms of the invention can include one or more contrast enhancing agents selected from an X-ray contrast agent, a CAT contrast agent, an ultrasound contrast agent and a magnetic resonance imaging contrast agent. Moreover, a phantom of the invention can include more than one type of contrast agent for the same or different imaging modalities.

Contrast agents are useful adjuncts in radiological imaging, making it possible to determine the location, size and conformation of organs or other structures of the body in the context of their surrounding tissues. Exemplary X-ray contrast agents include insoluble inorganic barium salts, which enhance X-ray attenuation in the body zones into which they distribute. Other X-ray contrast agents include soluble iodine containing compounds such as those marketed by Nycomed AS under the trade names Omnipaque® and Amipaque®. Much recent work on X-ray contrast agents has concentrated on aminopolycarboxylic acid (APCA) chelates of heavy metal ions.

Contrast agents for MR imaging are well-known in the art. MRI contrast agents are typically based on paramagnetic metal chelates or ferri- or ferro-magnetic particles. Chelates with high thermodynamic and kinetic stabilities are preferred since their ability to remain stable in vivo offers a distinct benefit to MR imaging and to the constructs of the present invention. Exemplary chelating agents include 1,4,7,10-tetraazacyclododecane-N,N',N",N'"-tetraacetic acid (DOTA). Further examples are 1,4,7,10-tetraazacyclododecane-N,N',N"-triacetic acid (DO3A), diethylene-triamine-pentaacetic acid (DTPA) and various analogs and derivatives of both ligands.

Chelated or unchelated paramagnetic metal ions are of use in the phantom of the invention. Paramagnetic metals of a wide range are suitable for complexation with these ligands. Suitable metals are those having atomic numbers of 22–29 (inclusive), 42, 44 and 58–70 (inclusive), and have oxidations states of 2 or 3. Those having atomic numbers of 22–29 (inclusive) and 58–70 (inclusive) are preferred, and those having atomic numbers of 24–29 (inclusive) and 64–68 (inclusive) are more preferred. Examples of such metals are chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III). Manganese (II), iron (III) and gadolinium (III) are particularly preferred, with gadolinium (III) the most preferred.

In a preferred embodiment, wherein the phantom is designed for use in conjunction with MR imaging, the contrast enhancing agent is a chelate of a paramagnetic lanthanide ion, which is preferably water soluble. The solution of chelate in the phantom generally has a concentration of from about 0.025M to about 2.5M.

The phantom of the invention can be configured to model various regions and tissues within a mammalian joint. In a preferred example, the phantom is configured to model articular cartilage of a mammalian joint, preferably a knee joint.

The phantom can be utilized to model any property of a constituent or array of constituents of the mammalian joint. For example, properties of articular cartilage that are modeled using a phantom of the invention include the thickness of the cartilage, the curvature of the cartilage and a combination thereof.

The phantom is intended to be imaged at regular intervals over the entire time period (e.g., months to years) that a given patient or group of patients is to be studied. The images and measurements derived from the phantom are used to check the accuracy and longitudinal precision of corresponding images and measurements derived from patients and correct them as necessary. Accurate measurements of known precision are essential in tracking small changes in disease state and response to therapy.

Phantom Types

The phantom of the present invention is of use in conjunction with an array of diagnostic and treatment modalities, including CT, MRI, ultrasound, x-ray and nuclear medicine. In each of the various modalities, the phantom of the invention is of use to test system performance, evaluate the repeatability of results obtained during the procedure, and compensate for any "drift" or change in the parameters of the procedure. Changes in procedure parameters arise from a variety of sources including, but not limited to, differences in patient characteristics, environmental sensitivity of the device, etc. The phantom of the invention is also of use in image quality control to, for example, compensate for noise, assess spatial resolution, sensitivity, slice thickness, focal zone, system sensitivity, gray scale, dynamic range, penetration, dead zone, dose, etc.

When the phantom of the invention is used in conjunction with a nuclear medicine procedure, the phantom is useful to assess the performance of gamma cameras (single photon emission computed tomography and positron emission tomography) for field uniformity, volume sensitivity, spatial resolution, lesion detectability, etc.

The phantom of the invention is useful for quality control, calibration and testing of radiographic, fluoroscopic, tomographic and angiographic equipment. The phantom is used to evaluate the system for contrast, resolution, image quality, image, intensifier performance, and exposure.

The phantom of the invention can also be used in conjunction with radiotherapy. The phantom is utilized to measure radiation dose, dose distributions, and other treatment parameters.

Figure 2A:
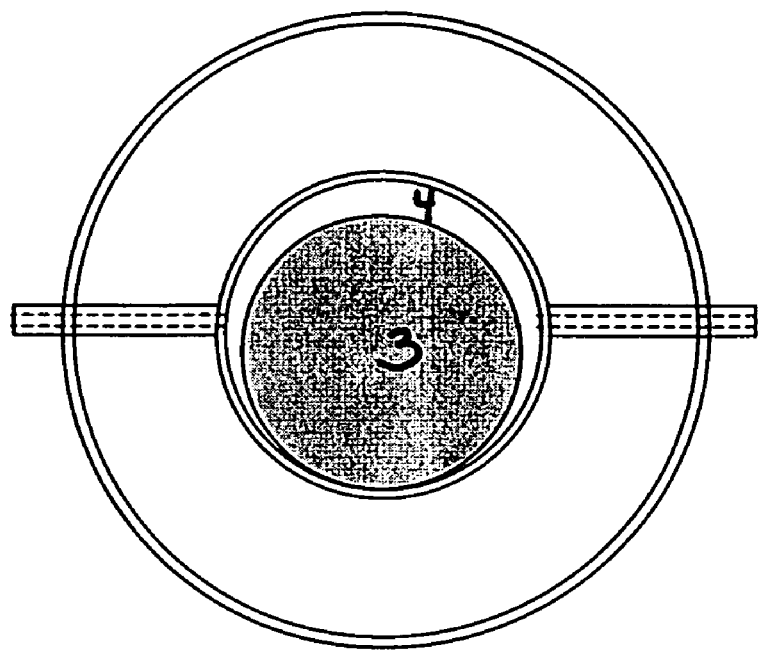
FIG. 2(A) an end view of a phantom including a cylindrical housing 1 through which two hollow rods 2 penetrate therethrough, connecting with a hollow sphere 4, within which is anchored a solid sphere (3); (B) is a top view of the same phantom.
Figure 2B:
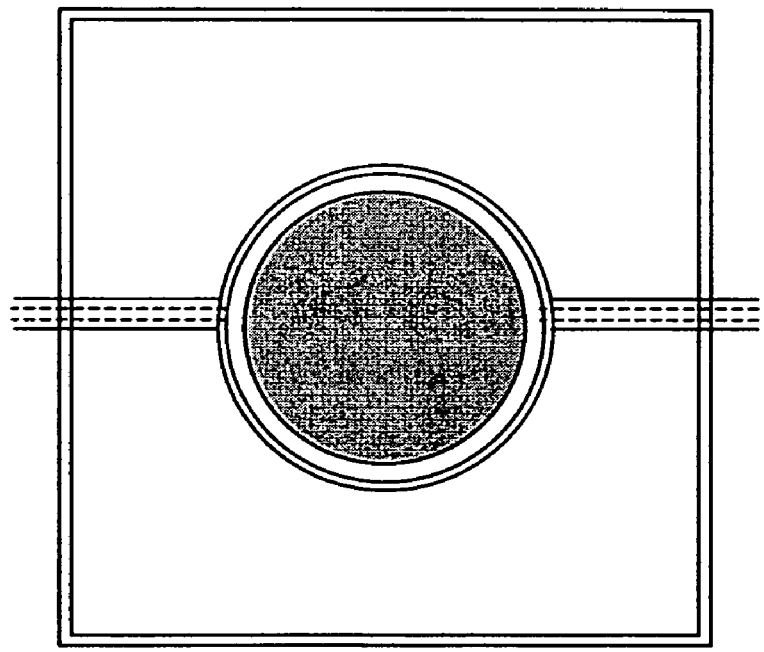

A presently preferred configuration of the phantom, useful in conjunction with MR imaging of the knee is displayed in FIG. 2. With reference to FIG. 2, the device includes an acrylic cylindrical housing 1. A hollow sphere is oriented inside the cylindrical housing and is held in place within the housing by means of a support member 2. The support member creates a conduit from the exterior of the housing to the interior of a hollow acrylic sphere 4. Within the hollow sphere, a solid sphere is anchored to a point on the inner surface of the hollow sphere. Further details of the configuration of an exemplary phantom of the invention are provided in the examples set forth hereinbelow.

The following examples are offered to illustrate a selected embodiment of the invention, not to limit the scope of the invention.

EXAMPLES

Example 1

Figure 3:
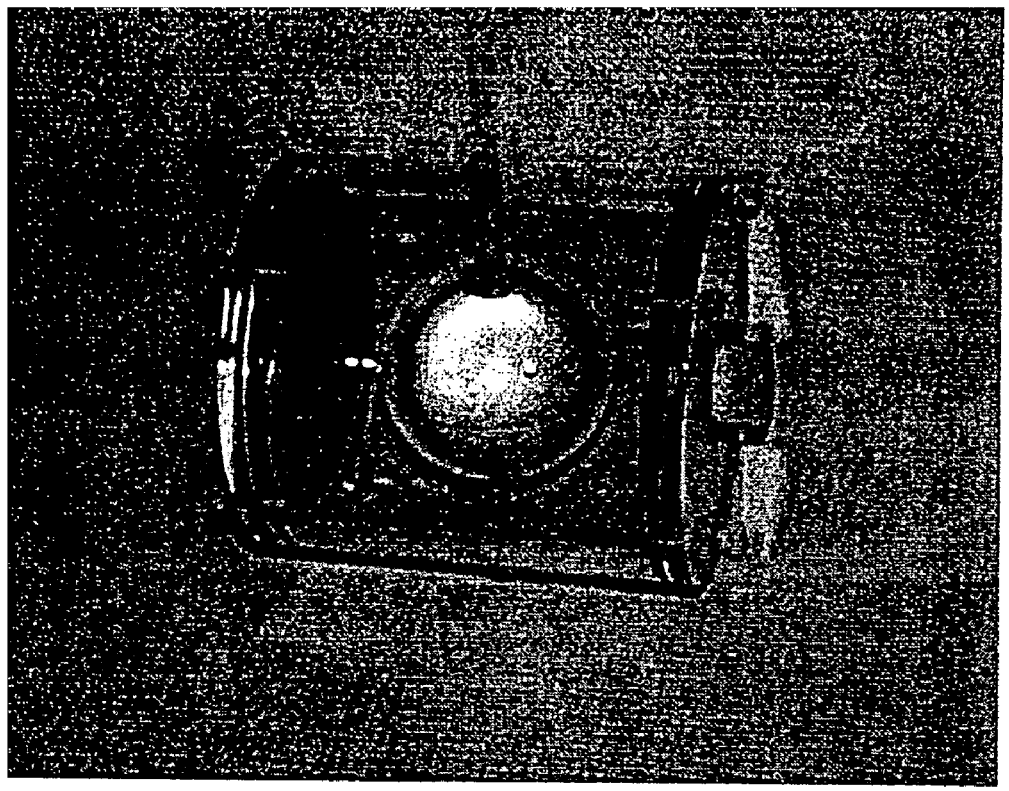
FIG. 3 is a photograph of an exemplary phantom of the invention.

The phantom is constructed of acrylic. The phantom shown in FIG. 2 consists of a 4 in. dia.×4 in. long (101.6 mm×101.6 mm) cylinder containing a hollow 2.25 in. (57.2 mm) i.d. sphere held in place by two hollow rods that communicate with the space inside the sphere. Attached to the inner wall of this sphere is a 2 in. (50.8 mm) dia. solid sphere. The dimension tolerance was 0.005 in. (0.1 mm). FIG. 3 is a photograph of the completed phantom. The hollow posts that support the outer, hollow sphere within the cylindrical body were used to completely fill the space between the solid inner sphere and the hollow outer sphere with distilled water. The weight of the water required divided by its density (0.998 at 22° C.; Handbook of Chemistry and Physics, CRC Press, Boca Raton, Fla.) gave its volume. For imaging, the water was replaced with 0.25 mM Gd-DTPA solution (Magnevist, Berlex Laboratories, Wayne, N.J.), and the body of the phantom was filled with distilled water.

Imaging was done using a 1.5 Tesla GE Signa LX system (GE Medical Systems, Milwaukee, Wis.) and an extremity coil (Medical Advances, Inc., Milwaukee, Wis.). The accuracy and precision of MRI spatial measurements are fundamentally determined by the magnetic field gradients that are used to encode this information in the image. The particular imager that was used in the method presented herein was serviced monthly by a GE Field Engineer who adjusted the gradients to within 0.5 mm in 100 mm, or 0.5%. The observed 1-pixel (0.5 mm) precision of in-plane measurements of the phantom agreed with this value. Likewise, the calculated slice thickness (2.00±0.09 mm) equaled the nominal slice thickness (2 mm).

A 3D-SPGR sequence (TR/TE/Flip 58 ms/6 ms/40°; 12 cm×12 cm FOV; 60 contiguous 2 mm slices; 256×192; 1 NEX) was used to obtain a set of images depicting the entire phantom in three dimensions.

The image data were transferred to a Sun workstation (Sun Microsystems, Palo Alto, Calif.) for display and analysis using MRVision software (MRVIsion, Inc., Wakefield, Mass.). To determine the volume of the annular space in the spherical phantom, ROI's in each slice of the 3D data set were manually segmented using a seed-growing algorithm, and the resulting area was multiplied by the slice thickness to yield the volume. This segmentation was repeated four times, and coefficients of variation (CV=mean/standard deviation) were calculated for the total volume, and for each slice.

Cross-sectional MR images of the phantom are shown in FIG. 4. The water-filled space between the two spheres appears as a high intensity crescent in those slices that pass through their point of contact, and an annulus or circle in other slices. The volume of this space determined from its contained mass of water was 30.1 cm$^3$±0.2 cm$^3$. Four replicate measurements of a single MRI data set gave values of 31.0, 29.7, 28.9, and 29.4 cm$^3$. The mean (sd) MRI volume was 29.8 cm$^3$ (0.9 cm$^3$), or 98.8% (3.0%) of the actual volume. The CV of the total volume was 3.03%. The slice root-mean-square CV was 9.35%.

In-plane linear measurements were accurate to one pixel, or 0.5 mm.

Example 2

Partial volume averaging is another source of error, especially when measuring a curved object using rectilinear voxels. However, the partial volume error can be calculated for this phantom, since its size and shape are precisely known. If one assumes ideal voxels of 0.5 mm×0.5 mm×2 mm and ideal segmentation*, the total voxel volume of a sphere of radius 24 mm is 99.98% of the true volume.

That is, all voxels whose centers lie within the sphere are counted as sphere. All voxels whose centers lie outside of the sphere are not counted, although they may contain part of the sphere. This corresponds to a segmentation threshold of about 50%.

The measured volume of the annular space (the model "cartilage") in the spherical phantom was 98.8%±3.0% of the true value. This total error (1.2%) is greater than the estimated partial volume error (0.02%) and comparable to the cumulative error in the gradients (3×0.5%=1.5%). These results can be used to calculate a correction factor (in this case, 1.02) and estimate a precision for in vivo measurements done at approximately the same time.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A phantom comprising:
   (a) a housing having an outside surface, an inside surface and a central axis defining a hollow region therein;
   (b) a hollow sphere oriented within said hollow region of said housing, having an inside surface defining a hollow spherical region therein;
   (c) a second sphere oriented inside said hollow sphere, anchored at one point to said inside surface of said hollow sphere, said second sphere having an outside surface defining a hollow region between said outside surface of said second sphere and said inside surface of said hollow sphere;
   (d) a stabilizing member joining said hollow sphere and said housing, said stabilizing member having a central axis defining a hollow region therein which communicates with said outside surface of said housing and said hollow region of said hollow sphere.

2. The phantom according to claim 1, wherein said second sphere is a member selected from hollow spheres and solid spheres.

3. The phantom according to claim 1, wherein a member selected from said hollow region of said hollow sphere, said second sphere and combinations thereof contains a liquid.

4. The phantom according to claim 1, wherein said second sphere and said hollow sphere contain a different liquid.

5. The phantom according to claim 1, wherein a member selected from said hollow region of said hollow sphere, said second sphere and combinations thereof contains a member selected from the group consisting of air, distilled water, a solution of a contrast enhancing agent, a suspension of a contrast enhancing agent and combinations thereof.

6. The phantom according to claim 5, wherein said contrast enhancing agent is a member selected from an X-ray contrast agent, a CAT contrast agent, an ultrasound contrast agent and a magnetic resonance imaging contrast agent.

7. The phantom according to claim 6, wherein said contrast enhancing agent is a chelate of a paramagnetic lanthanide ion.

8. The phantom according to claim 7, wherein said chelate of a paramagnetic lanthanide ion is present in a concentration of from about 0.025M to about 2.5M.

9. The phantom according to claim 1, configured to model articular cartilage of a mammalian joint.

10. The phantom according to claim 9, wherein said joint is a knee joint.

11. The phantom according to claim 9, wherein a member selected from thickness of said cartilage, curvature of said cartilage and a combination thereof is modeled.

* * * * *